United States Patent [19]

Su et al.

[11] Patent Number: 4,775,678

[45] Date of Patent: Oct. 4, 1988

[54] CLOTRIMAZOLE CREAM

[75] Inventors: Ching-Chiang Su, Portage, Mich.; Joel A. Sequeira, New York, N.Y.

[73] Assignee: Schering Corporation, Kenilworth, N.J.

[21] Appl. No.: 861,021

[22] Filed: May 8, 1986

Related U.S. Application Data

[63] Continuation-in-part of Ser. No. 656,217, Oct. 1, 1984, abandoned.

[51] Int. Cl.⁴ .............................. H61K 31/415
[52] U.S. Cl. ................................ 514/396; 514/947
[58] Field of Search .......................... 514/396

[56] References Cited

U.S. PATENT DOCUMENTS 3,660,577  5/1972  Buchel et al. .................. 424/273
4,444,762  4/1984  Rajadhyaksha ................. 424/180

OTHER PUBLICATIONS

Physicians Desk Reference, 31st ed., 1977, p. 750.

*Primary Examiner*—Leonard Schenkman
*Attorney, Agent, or Firm*—Gerald S. Rosen; Stephen I. Miller; Thomas D. Hoffman

[57] ABSTRACT

An oil-in-water cream or lotion emulsion formulation containing clotrimazole having improved antifungal properties containing various amounts of clotrimazole, petrolatum, cetearyl alcohol, propylene glycol, and ceteth-20, with or without other additional ingredients.

3 Claims, 1 Drawing Sheet

Per cent efficacy versus per cent drug concentration: ●- Clotrimazole in the claimed oil/water emulsion cream base; ▲- Clotrimazole in a commercial oil/water cream base. Per cent efficacy is plotted on a probit scale and is based on area under the curve measurements, AUC.

Per cent efficacy versus per cent drug concentration: ● - Clotrimazole in the claimed oil/water emulsion cream base; ▲ - Clotrimazole in a commercial oil/water cream base. Per cent efficacy is plotted on a probit scale and is based on area under the curve measurements, AUC.

CLOTRIMAZOLE CREAM

This application is a continuation-in-part of applicant's co-pending U.S. patent application Ser. No. 656,217, filed Oct. 1, 1984 abandoned.

BACKGROUND

This invention relates to a cream or lotion formulation of clotrimazole having improved antifungal properties and superior penetrating properties.

CLotrimazole, 1-[(2-chlorophenyl)diphenylmethyl]-1H-imidazole, described in U.S. Pat. No. 3,660,577, is an effective antifungal compound. However, to be optimally effective it must be brought into direct contact with the fungal infection being treated. Unfortunately, such infections are frequently located in hard to reach deeper skin layers, hyper-keratinized skin and/or nails. Hence, a clotrimazole containing formulation having a high degree of penetration enabling it to reach hard-to-reach fungal infections is highly desirable.

SUMMARY

The present invention provides antifungal percutaneous cream or lotion compositions, for administration to warm-blooded animals, including man, containing as the active antifungal ingredient an antifungal effective amount of clotrimazole. The compositions have superior penetrating properties, enhanced antifungal activity, and are optimally effective at a pH range of 5-7.

In addition to the active ingredient, clotrimazole, a specific combination of pharmaceutically acceptable adjuvants are in the formulation of this invention. The adjuvants must be chemically inert to the remaining ingredients.

The compositions with superior penetrating powers contain an innocuous vehicle with emollient occlusive properties, e.g., petrolatum; a bodying agent which gives a good feel on the skin, e.g., cetearyl alcohol, cetyl alcohol, stearyl alcohol, stearic acid and the like, with cetearyl alcohol preferred; a solubility enhancer for clotrimazole, e.g., propylene glycol, hexylene glycol, polyethylene glycol 400 and the like, with propylene glycol preferred; and a non-ionic surfactant which forms an oil-in-water emulsion cream base, e.g., ceteth 20, steareth-2, steareth-20 or mixtures thereof and the like, with ceteth 20 preferred; and water.

Optional ingredients in the compositions of this invention are buffers such as mono- and di-basic sodium phosphate, mineral oil, preservatives such as benzyl alcohol, stabilizers and other conventional excipients for topical creams and lotions so long as they do not deleteriously affect the penetrating properties.

The antifungal activity of the composition of this invention is about 2 to 3 times greater than is manifested by known clotrimazole containing compositions. The following are illustrative formulations of this invention:

---

I. (a) 0.1 to 100 mg clotrimazole;
   (b) 100 to 300 mg petrolatum;
   (c) 50 to 120 mg cetearyl alcohol;
   (d) 50 to 200 mg propylene glycol;
   (e) 15 to 30 mg ceteth-20; and
   (f) water q.s. to 1 gram.
II. 5 to 50 mg clotrimazole;
   150 to 200 mg petrolatum;
   60 to 80 mg cetearyl alcohol;
   90 to 110 mg propylene glycol;
   20 to 25 mg ceteth-20; and
   water q.s. to 1 gram.
III. 40 mg clotrimazole;
   150 mg petrolatum;
   72 mg cetearyl alcohol;
   22.5 mg ceteth-20;
   100 mg propylene glycol; and
   water q.s. to 1 gram.
IV. 30 mg clotrimazole;
   150 mg petrolatum;
   72 mg cetearyl alcohol;
   100 mg propylene glycol;
   22.5 mg ceteth-20;

--- additional ingredients selected from the group consisting of 60 mg/g mineral oil, 10 mg/g benzyl alcohol, 0.35 mg/g anhydrous dibasic sodium phosphate, 5 mg/g monobasic sodium phosphate and combinations thereof; and water q.s. to 1 gram.

---

V. 20 mg clotrimazole;
   150 mg petrolatum;
   72 mg cetearyl alcohol;
   100 mg propylene glycol;
   22.5 mg ceteth-20;
   60 mg mineral oil;
   10 mg benzyl alcohol;
   0.35 mg anhydrous dibasic sodium phosphate;
   5 mg monobasic sodium phosphate; and
   water q.s. to 1 gram.
VI. 50 mg clotrimazole;
   150 mg petrolatum;
   24 mg cetearyl alcohol;
   100 mg propylene glycol;
   22.5 mg ceteth-20; and
   water q.s. to 1 gram.
VII. 100 mg clotrimazole;
   150 mg petrolatum;
   24 mg cetearyl alcohol;
   100 mg propylene glycol;
   22.5 mg ceteth-20;

--- additional ingredients selected from the group consisting of 20 mg/g mineral oil, 10 mg/g benzyl alcohol, 0.35 mg/g anhydrous dibasic sodium phosphate, 5 mg/g monobasic sodium phosphate and combination thereof; and water q.s. to 1 gram.

---

VIII. 40 mg clotrimazole;
   150 mg petrolatum;
   24 mg cetearyl alcohol;
   100 mg propylene glycol;
   22.5 mg ceteth-20;
   20 mg mineral oil;
   10 mg benzyl alcohol;
   0.35 mg anhydrous dibasic sodium phosphate;
   5 mg monobasic sodium phosphate; and
   water q.s. to 1 gram.
IX. 0.1 to 100 mg clotrimazole;
   100 to 300 mg petrolatum;
   50 to 120 mg cetearyl alcohol;
   50 to 200 mg propylene glycol;
   15 to 30 mg ceteth-20;
   10 mg/g preservative exclusive of benzyl alcohol; and
   water q.s. to 1 gram.
X. 0.1 to 100 mg clotrimazole;
   100 to 300 mg petrolatum;
   50 to 120 mg cetearyl alcohol;
   50 to 200 mg propylene glycol;
   15 to 30 mg ceteth-20;
   15-30 mg/g steareth-2 (Brij 72) and 15-30 mg/g steareth-20 (Brij 78); and -continued water q.s. to 1 gram.
XI. 40 mg clotrimazole;
150 mg petrolatum;
24 mg cetearyl alcohol;
100 mg propylene glycol;
22.5 mg ceteth-20;
0.5–5 mg/g buffer of citrate/sodium hydroxide and citrate/phosphate; and
water q.s. to 1 gram.
XII. 0.1 to 100 mg clotrimazole;
100 to 300 mg petrolatum;
50 to 120 mg cetearyl alcohol;
50 to 200 mg propylene glycol;
15 to 30 mg ceteth-20;
0.5–5 mg/g buffer of citrate/sodium hydroxide and citrate/phosphate; and
water q.s. to 1 gram.
XIII. 70 mg clotrimazole;
150 mg petrolatum;
24 mg cetearyl alcohol;
100 mg propylene glycol;
22.5 mg ceteth-20;
22.5 mg/g Brij 72 and 22.5 mg/g Brij 78; and
water q.s. to 1 gram.
XIV. 40 mg clotrimazole;
150 mg petrolatum;
24 mg cetearyl alcohol;
100 mg propylene glycol;
22.5 mg ceteth-20;
10 mg/g preservative exclusive of benzyl alcohol; and
water q.s. to 1 gram.
XV. 40 mg clotrimazole;
150 mg petrolatum;
72 mg cetearyl alcohol;
100 mg propylene glycol;
22.5 mg ceteth-20;
60 mg mineral oil;
10 mg benzyl alcohol;
0.35 mg anhydrous dibasic sodium phosphate;
5 mg monobasic sodium phosphate; and
water q.s. to 1 gram.
XVI. 0.5 mg clotrimazole;
150 mg petrolatum;
72 mg cetearyl alcohol;
100 mg propylene glycol;
22.5 mg ceteth-20;
60 mg mineral oil;
10 mg benzyl alcohol;
0.35 mg anhydrous dibasic sodium phosphate;
5 mg monobasic sodium phosphate; and
water q.s. to 1 gram.
XVII. 0.1 mg clotrimazole;
150 mg petrolatum;
72 mg cetearyl alcohol;
100 mg propylene glycol;
22.5 mg ceteth-20;
60 mg mineral oil;
10 mg benzyl alcohol;
0.35 mg anhydrous dibasic sodium phosphate;
5 mg monobasic sodium phosphate; and
water q.s. to 1 gram.

As used herein:

"Cetearyl alcohol" is defined as a mixture of fatty alcohols consisting predominantly of cetyl and stearyl alcohols.

"Ceteth-20" is defined as having the polyethylene glycol ether of cetyl alcohol (q.v.) that conforms to the formula $CH_3(CH_2)_{14}CH_2(OCH_2CH_2)_nOH$ where n has an average value of 20.

"Brij 72" is "steareth-2" which is defined as the polyethylene glycol ether of stearyl alcohol (q.v.) that conforms to the formula:

$$CH_3(CH_2)_{16}CH_2(OCH_2CH_2)_nOH$$

where n has an average value of 2.

"Brij 78" is "steareth-20" which is defined as the polyethylene glycol ether of stearyl alcohol (q.v.) that conforms to the formula:

$$CH_3(CH_2)_{16}CH_2(OCH_2CH_2)_nOH$$

where n has an average value of 20.

Except for "clotrimazole" and water, all ingredients appearing in the specification and claims are defined in the CTFA Cosmetic Ingredient Dictionary, 3rd Edition, (1982), published by the Cosmetic, Toiletry and Fragrance Association, Inc. which is incorporated herein by reference.

DETAILED DESCRIPTION OF THE INVENTION

Figure 1:
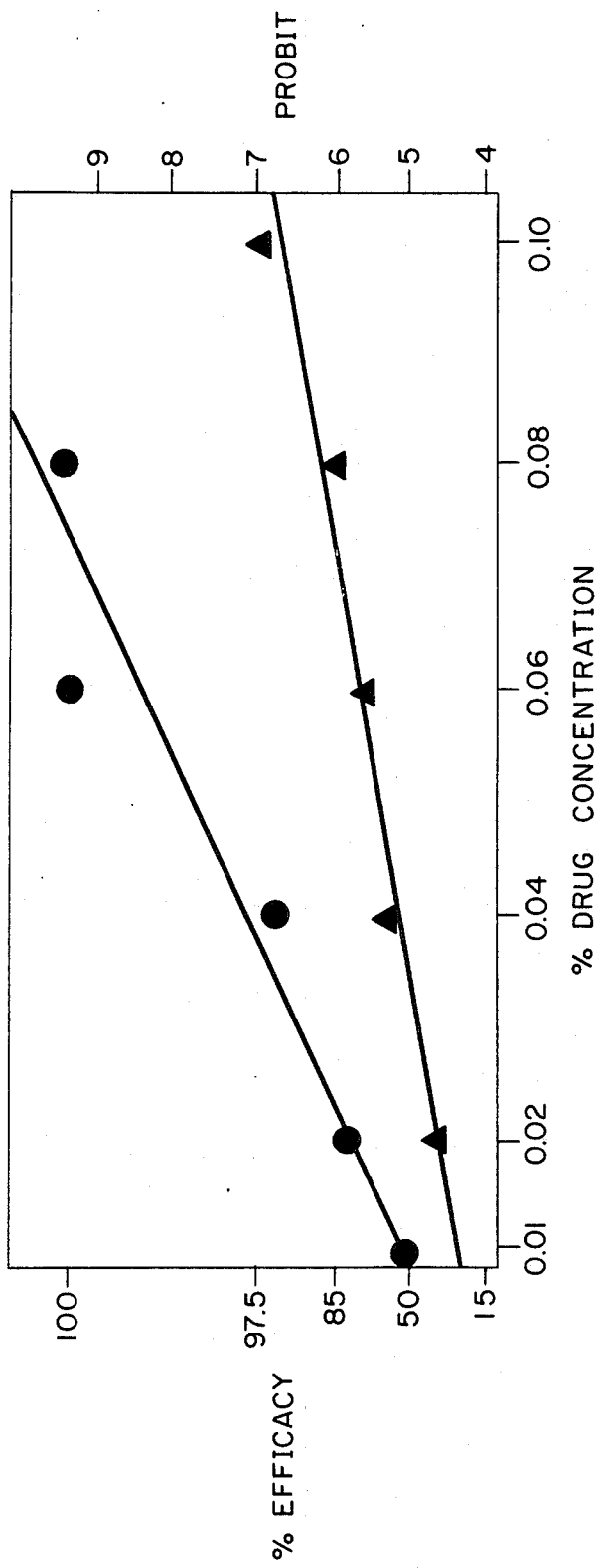
FIG. 1 is a graph of the % efficacy based on the area under the curve vs. % concentration of clotrimazole in the claimed oil-in-water composition and in the commercial oil-in-water composition.

The antifungal topical cream or lotion compositions of this invention contain about 0.1 to 100 mg/g, preferably about 10 to 30 mg/g, of clotrimazole as the active antifungal ingredient and as the combination of ingredients which are responsible for the superior penetrating properties and thus enhanced antifungal activity per unit of clotrimazole, about 100 to 300 mg/g of petrolatum, preferably 150 to 200 mg/g; about 50 to 120 mg/g of a bodying agent which imparts good feel, preferably about 60 to 80 mg/g, the preferred bodying agent is cetearyl alcohol; about 50 to 200 mg/g of a solubility and preservative enhancer, preferably about 90 to 100 mg/g, the preferred enhancer is propylene glycol; about 15 to 30 mg/g of a non-ionic surfactant which forms an oil-in-water emulsion cream base, preferably 20 to 25 mg/g, the preferred surfactant is ceteth-20.

Other optional ingredients can be added to act as preservatives, pH controllers, perfumes and the like. Typical suitable optional ingredients are mineral oil, about 20–60 mg/g; benzyl alcohol, about 10 mg/g; anhydrous dibasic sodium phosphate, about 0.35 mg/g; monobasic sodium phosphate, about 5 mg/g; about 10 mg/g of preservatives other than benzyl alcohol, e.g., sorbic acid, benzoic acid, methyl and ethyl parabens and the like; about 15–30 mg/g of Brij 72 and Brij 78; about 0.5–5 mg/g of a buffer of sodium citrate/sodium hydroxide and sodium citrate/mono- and dibasic sodium phosphate, to maintain the pH within the preferred range of about 5–7 pH.

The preferred essential ingredients and amounts thereof as shown below in Table I form anti-fungal oil-in-water emulsion creams which creams are cutaneously penetrating and impart enhanced antifungal activity.

TABLE I

TOPICAL ANTI-FUNGAL OIL-IN-WATER PENETRATING BASE

| Ingredients | Operable Concentration mg/g of the Formulation | Preferred Concentration mg/g of the Formulation |
|---|---|---|
| Clotrimazole | 0.1 to 100 | 30 to 50 |
| Petrolatum | 100 to 300 | 150 to 200 |
| Cetearyl Alcohol | 50 to 120 | 60 to 80 |
| Propylene Glycol | 50 to 200 | 90 to 110 |
| Ceteth 20 | 15 to 30 | 20 to 25 |

TABLE I-continued

TOPICAL ANTI-FUNGAL OIL-IN-WATER PENETRATING BASE

| Ingredients | Operable Concentration mg/g of the Formulation | Preferred Concentration mg/g of the Formulation |
|---|---|---|
| Water | q.s. for 1 gram | q.s. for 1 gram |

Clotrimazole formulated in the oil-in-water emulsion cream bases (Table I) and in a commercial oil-in-water emulsion cream base, i.e. the antifungal cream "Lotrimin" marketed by Schering-Plough of the following composition

| Ingredient | mg/g |
|---|---|
| Clotrimazole | 0.2-1.0 |
| Cetyl esters wax | 30.0 |
| Cetearyl Alcohol | 100.0 |
| Sorbitan Monostearate | 20.0 |
| Polysorbate 60* | 15.0 |
| Octyl Dodecanol | 135.00 |
| Benzyl Alcohol | 10.00 |
| purified water q.s. to 1.0 g | |

*(Polysorbate 60 is a mixture of stearate esters of sorbitol and sorbitol anhydrides, consisting predominately of the monoester, condensed with approximately 20 moles of ethylene oxide)

were tested topically at five concentrations in a guinea pig dermatophyte model against *Trichophyton mentagrophytes*. Seven animals per concentration were infected with *T. mentagrophytes* and then treated with the commercial cream base or a cream base within the scope of those in Table I. The infected areas were cultured, and the plates were examined after four and eight days incubation. The cultures were scored as 0 if negative after eight days, as 2 if positive after four days and as 1 if negative after four days and positive after eight days. The percent cultures negative were calculated daily for each group as $$1 - \frac{\text{score}}{\text{maximum possible score}} \times 100.$$

These data are presented in Tables II and III. For both groups, graphs of percent cultures negative versus time were prepared. The areas under the curves (AUC's) were calculated by the trapezoidal rule. The AUC divided by the maximum possible AUC×100 was also calculated to give the percent AUC. A probit analysis of the percent AUC versus dose was used to determine the $ED_{90}$ (see FIG. 1 and Table IV).

TABLE II

SCORES WITH 0.1%–0.02% CLOTRIMAZOLE IN THE KNOWN COMMERCIAL OIL-IN-WATER EMULSION CREAM BASE FORMULATION

| 0.1% | | | | | | | | 0.08% | | | | | | | |
|---|---|---|---|---|---|---|---|---|---|---|---|---|---|---|---|
| day | 7 animals | | | | | | Score | day | 7 animals | | | | | | Score |
| 2 | 0 | 0 | 1 | 0 | 0 | 0 | 1 | 86 | 2 | 1 | 1 | 1 | 2 | 0 | 0 | 0 | 64 |
| 4 | 0 | 0 | 0 | 0 | 0 | 1 | 0 | 93 | 4 | 0 | 0 | 1 | 0 | 1 | 1 | 2 | 64 |
| 7 | 0 | 0 | 0 | 0 | 0 | 0 | 0 | 100 | 7 | 0 | 1 | 1 | 0 | 0 | 0 | 0 | 86 |
| 9 | 0 | 0 | 0 | 0 | 0 | 0 | 0 | 100 | 9 | 0 | 0 | 1 | 1 | 0 | 0 | 0 | 86 |
| 11 | 0 | 0 | 0 | 0 | 0 | 0 | 0 | 100 | 11 | 0 | 1 | 1 | 0 | 0 | 0 | 0 | 86 |
| 14 | 0 | 0 | 0 | 0 | 0 | 0 | 0 | 100 | 14 | 0 | 0 | 0 | 0 | 0 | 0 | 0 | 100 |
| 16 | 0 | 0 | 0 | 0 | 0 | 0 | 0 | 100 | 16 | 0 | 0 | 0 | 0 | 0 | 0 | 1 | 93 |

| 0.06% | | | | | | | | 0.04% | | | | | | | |
|---|---|---|---|---|---|---|---|---|---|---|---|---|---|---|---|
| day | 7 animals | | | | | | Score | day | 7 animals | | | | | | Score |
| 2 | 0 | 1 | 1 | 1 | 1 | 0 | 2 | 57 | 2 | 2 | 2 | 2 | 2 | 2 | 2 | 2 | 0 |
| 4 | 1 | 2 | 1 | 2 | 2 | 2 | 1 | 21 | 4 | 2 | 2 | 2 | 2 | 2 | 2 | 2 | 0 |
| 7 | 0 | 0 | 1 | 1 | 0 | 0 | 0 | 86 | 7 | 0 | 0 | 2 | 0 | 0 | 0 | 0 | 86 |
| 9 | 0 | 1 | 2 | 2 | 0 | 0 | 0 | 64 | 9 | 0 | 0 | 2 | 0 | 0 | 0 | 2 | 71 |
| 11 | 0 | 0 | 1 | 0 | 0 | 0 | 0 | 93 | 11 | 0 | 0 | 0 | 0 | 0 | 0 | 0 | 100 |
| 14 | 0 | 0 | 0 | 0 | 0 | 0 | 0 | 100 | 14 | 0 | 0 | 0 | 0 | 0 | 0 | 0 | 100 |
| 16 | 0 | 2 | 0 | 0 | 0 | 0 | 0 | 86 | 16 | 0 | 0 | 2 | 0 | 0 | 1 | 2 | 64 |

| 0.02% | | | | | | | |
|---|---|---|---|---|---|---|---|
| day | 7 animals | | | | | | Score |
| 2 | 2 | 2 | 2 | 2 | 2 | 2 | 2 | 0 |
| 4 | 2 | 2 | 2 | 2 | 2 | 2 | 2 | 0 |
| 7 | 0 | 2 | 2 | 0 | 2 | 2 | 2 | 29 |
| 9 | 2 | 2 | 2 | 2 | 2 | 2 | 2 | 0 |
| 11 | 0 | 0 | 0 | 0 | 0 | 0 | 2 | 86 |
| 14 | 0 | 0 | 0 | 0 | 0 | 0 | 0 | 100 |
| 16 | 0 | 2 | 2 | 0 | 0 | 0 | 0 | 57 |

TABLE III

SCORES WITH 0.08%–0.01% CLOTRIMAZOLE IN THE OIL-IN-WATER EMULSION CREAM BASE FORMULATIONS OF THIS INVENTION

| 0.08% | | | | | | | | 0.06% | | | | | | | |
|---|---|---|---|---|---|---|---|---|---|---|---|---|---|---|---|
| day | 7 animals | | | | | | Score | day | 7 animals | | | | | | Score |
| 2 | 0 | 0 | 0 | 0 | 0 | 0 | 0 | 100 | 2 | 0 | 0 | 0 | 0 | 0 | 0 | 0 | 100 |
| 4 | 0 | 0 | 0 | 0 | 0 | 0 | 0 | 100 | 4 | 0 | 0 | 0 | 0 | 0 | 0 | 0 | 100 |
| 7 | 0 | 0 | 0 | 0 | 0 | 0 | 0 | 100 | 7 | 0 | 0 | 0 | 0 | 0 | 0 | 0 | 100 |
| 9 | 0 | 0 | 0 | 0 | 0 | 0 | 0 | 100 | 9 | 0 | 0 | 0 | 0 | 0 | 0 | 0 | 100 |
| 11 | 0 | 0 | 0 | 0 | 0 | 0 | 0 | 100 | 11 | 0 | 0 | 0 | 0 | 0 | 0 | 0 | 100 |
| 14 | 0 | 0 | 0 | 0 | 0 | 0 | 0 | 100 | 14 | 0 | 0 | 0 | 0 | 0 | 0 | 0 | 100 |
| 16 | 0 | 0 | 0 | 0 | 0 | 0 | 0 | 100 | 16 | 0 | 0 | 0 | 0 | 0 | 0 | 0 | 100 |

TABLE III-continued
SCORES WITH 0.08%-0.01% CLOTRIMAZOLE IN THE OIL-IN-WATER EMULSION CREAM BASE FORMULATIONS OF THIS INVENTION

| 0.04% | | | | | | | | | 0.02% | | | | | | | | |
|---|---|---|---|---|---|---|---|---|---|---|---|---|---|---|---|---|---|
| day | 7 animals | | | | | | | Score | day | 7 animals | | | | | | | Score |
| 2 | 0 | 1 | 1 | 0 | 0 | 0 | 1 | 79 | 2 | 2 | 2 | 2 | 2 | 1 | 2 | 0 | 21 |
| 4 | 0 | 0 | 0 | 0 | 0 | 0 | 1 | 93 | 4 | 0 | 0 | 0 | 0 | 1 | 0 | 1 | 86 |
| 7 | 0 | 0 | 0 | 0 | 0 | 0 | 0 | 100 | 7 | 1 | 2 | 1 | 0 | 0 | 0 | 0 | 71 |
| 9 | 0 | 0 | 0 | 0 | 0 | 0 | 0 | 100 | 9 | 0 | 0 | 0 | 0 | 0 | 0 | 0 | 100 |
| 11 | 0 | 0 | 0 | 0 | 0 | 0 | 0 | 100 | 11 | 0 | 0 | 0 | 1 | 0 | 1 | 0 | 86 |
| 14 | 0 | 0 | 0 | 0 | 0 | 0 | 0 | 100 | 14 | 0 | 0 | 0 | 0 | 0 | 0 | 0 | 100 |
| 16 | 0 | 0 | 0 | 0 | 0 | 0 | 0 | 100 | 16 | 0 | 0 | 0 | 0 | 0 | 0 | 0 | 100 |

| 0.01% | | | | | | | | |
|---|---|---|---|---|---|---|---|---|
| day | 7 animals | | | | | | | Score |
| 2 | 2 | 2 | 2 | 2 | 2 | 2 | 2 | 0 |
| 4 | 2 | 1 | 2 | 2 | 0 | 2 | 0 | 36 |
| 7 | 2 | 2 | 1 | 2 | 2 | 1 | 2 | 14 |
| 9 | 1 | 0 | 0 | 2 | 0 | 2 | 0 | 64 |
| 11 | 0 | 0 | 0 | 0 | 0 | 0 | 0 | 100 |
| 14 | 0 | 0 | 0 | 0 | 0 | 0 | 0 | 100 |
| 16 | 0 | 0 | 0 | 0 | 0 | 2 | 0 | 86 |

TABLE IV
IN VIVO ANTIFUNGAL POTENCY IN THE GUINEA PIG DERMATOPHYTE MODEL

| Vehicle | $ED_{90}$ (%) Dose | |
|---|---|---|
| | Exp. 1 | Exp. 2 |
| Commercial oil-in-water emulsion cream base | 0.095 | 0.060 |
| Cream base of this invention | 0.029 | 0.027 |

As can be noted above (FIG. 1 and Table IV), clotrimazole in the cream base formulation of this invention exhibits about 2 to 3 times greater in vivo potency when topically applied than the same dose of clotrimazole administered in a commercial oil-in-water emulsion cream base formulation.

Optional additional pharmaceutically acceptable ingredients can be included in the composition of this invention such as: mineral oil, benzyl alcohol, anhydrous dibasic sodium phosphate, monobasic sodium phosphate, and other commonly used buffers and preservatives. The pH of the formulation is most preferable at a pH range of 5-7.

The following examples illustrate the invention.

EXAMPLE I

An oil-in-water antifungal cream emulsion, i.e. a spreadable semi-solid, is prepared from the following ingredients:

| Ingredient | Amount (mg/g) |
|---|---|
| Clotrimazole | 40.00 |
| White petrolatum, USP | 150.00 |
| Mineral oil, USP | 60.00 |
| Cetearyl alcohol | 72.00 |
| Ceteth 20 | 22.50 |
| Benzyl alcohol, NF | 10.00 |
| Propylene glycol, USP | 100.00 |
| Anhydrous dibasic sodium phosphate | 0.35 |
| Monobasic sodium phosphate monohydrate | 5.00 |
| Water | q.s. to 1 g |

Procedure

Heat 75% of the water to 70° C. in a suitable vessel. Add the monobasic sodium phosphate monohydrate, anhydrous dibasic sodium phosphate, propylene glycol, and benzyl alcohol to the vessel with agitation, maintaining the temperature at 70° C.

In a separate vessel, melt the petrolatum and heat to 70° C. Add the mineral oil and mix. Add the cetearyl alcohol and 95% of the ceteth 20; mix and maintain 70° C.

Combine the contents of the 2 vessels with agitation, maintaining 70° C.

Cool to 38° C. with agitation.

In a separate vessel dissolve the remaining ceteth 20 in the remaining water at 65° C. with agitation. Cool to room temperature and slurry the clotrimazole with vigorous agitation until a smooth uniform slurry is obtained.

Add the slurry to the previous emulsion mixture and agitate while cooling to room temperature.

EXAMPLE II

An oil-in-water emulsion in the form of a liquid antifungal lotion is prepared from the following ingredients:

| Ingredient | Amount (mg/g) |
|---|---|
| Clotrimazole | 40.00 |
| White petrolatum, USP | 50.00 |
| Mineral oil, USP | 20.00 |
| Cetearyl alcohol | 24.00 |
| Ceteth 20 | 22.50 |
| Benzyl alcohol, NF | 10.00 |
| Propylene glycol, USP | 100.00 |
| Anhydrous dibasic sodium phosphate | 0.35 |
| Monobasic sodium phosphate, monohydrate | 5.00 |
| Water | q.s. for 1 g |

The ingredients are combined according to the procedure for Example I.

Formulations I through XVII are prepared according to the procedure for Example I.

What is claimed is:

1. An oil-in-water cream base antifungal percutaneous composition comprising:

0.5 mg clotrimazole;
150 mg petrolatum;
72 mg cetearyl alcohol;

-continued 100 mg propylene glycol;
22.5 mg ceteth-20
60 mg mineral oil
10 mg benzyl alcohol;
0.35 mg anhydrous dibasic sodium phosphate;
5 mg monobasic sodium phosphate; and
water q.s. to 1 gram.

2. An oil-in-water cream base anti-fungal percutaneous composition comprising:

0.1 mg clotrimazole;
150 mg petrolatum;
72 mg cetearyl alcohol;
100 mg propylene glycol;
22.5 mg ceteth-20;

-continued 60 mg mineral oil;
10 mg benzyl alcohol;
0.35 mg anhydrous dibasic sodium phosphate;
5 mg monobasic sodium phosphate; and
water q.s. to 1 gram 3. An oil-in-water cream base antifungal percutaneous composition comprising the following ingredients in the indicated proportions:

(a) 0.1 to 100 mg clotrimazole;
(b) 100 to 300 mg petrolatum;
(c) 50 to 120 mg cetearyl alcohol;
(d) 50 to 200 mg propylene glycol;
(e) 15 to 30 mg ceteth 20; and
(f) pharmaceutically acceptable aqueous solvents to 1 gram.

* * * * *